United States Patent
Ishihara et al.

(10) Patent No.: US 7,301,045 B2
(45) Date of Patent: Nov. 27, 2007

(54) METHOD FOR PREPARING ESTER CONDENSATE

(75) Inventors: Kazuaki Ishihara, Konan (JP); Hisashi Yamamoto, Nagoya (JP)

(73) Assignee: Japan Science and Technology Corporation, Kawaguchi-Shi, Saitama (JP)

( * ) Notice: Subject to any disclaimer, the term of this patent is extended or adjusted under 35 U.S.C. 154(b) by 0 days.

(21) Appl. No.: 10/399,233

(22) PCT Filed: Aug. 23, 2001

(86) PCT No.: PCT/JP01/07195

§ 371 (c)(1),
(2), (4) Date: Apr. 14, 2003

(87) PCT Pub. No.: WO02/36538

PCT Pub. Date: May 10, 2002

(65) Prior Publication Data

US 2004/0015005 A1    Jan. 22, 2004

(30) Foreign Application Priority Data

Oct. 16, 2000    (JP)    .............................. 2000-314712

(51) Int. Cl.
*C07C 69/74* (2006.01)
*C07C 69/76* (2006.01)
*C07C 321/00* (2006.01)

(52) U.S. Cl. ................... 560/1; 560/9; 560/15; 560/81

(58) Field of Classification Search .............. 560/1, 560/9, 15, 81
See application file for complete search history.

(56) References Cited

U.S. PATENT DOCUMENTS 5,004,820 A * 4/1991 Buchwald et al. ............. 556/53

(Continued)

FOREIGN PATENT DOCUMENTS

EP    1 227 077 A2    7/2002

(Continued)

OTHER PUBLICATIONS

Barraclough et al., "The Infrared Spectra of Some Metal Alkoxides, Triallcylsilyloxides, and Related Silanols", *Journal of the Chemical Society*, Part III, pp. 2601-4268, 1961.

(Continued)

*Primary Examiner*—Taylor Victor Oh
(74) *Attorney, Agent, or Firm*—Morgan & Finnegan, L.L.P.

(57) ABSTRACT

The present invention provides a method for preparing ester or thioester that can conduct catalytic esterification reaction with an equimolar amount of carboxylic acid and alcohol, or catalytic thioesterification reaction with carboxylic acid and an equimolar amount or small amount of thiol, and can be expected as an industrial method that needs an enormous amount of synthesis in the light of green chemistry. By using hafnium chloride (IV), especially tetravalent hafnium compounds represented by hafnium chloride (IV)·(THF)$_2$ or hafnium (IV)t-butoxide as a (poly) condensation catalyst, direct condensation reaction is conducted from carboxylic acid and an equimolar amount of alcohol or a little smaller amount of thiol, in the nonpolar solvent such as toluene and the like, in a deoxidization atmosphere and under heating reflux, and the reaction synthesizes ester monomer or thioester monomer, polyester or polythioester. When heating reflux is conducted by using a nonpolar solvent, it is preferable to remove azeotropic water from the reaction system.

3 Claims, 1 Drawing Sheet

U.S. PATENT DOCUMENTS 5,760,265 A 6/1998 Takahara et al.
6,013,745 A 1/2000 McKay et al.
6,278,015 B1 * 8/2001 Spangler et al. ............ 560/227

FOREIGN PATENT DOCUMENTS

| | | |
|---|---|---|
| JP | 4-1156 | 1/1992 |
| JP | 5-286894 | 11/1993 |
| JP | 8-71429 | 3/1996 |
| JP | 08-071429 * | 3/1996 |
| JP | 10-310557 | 11/1998 |
| JP | 2000-154241 * | 6/2000 |

OTHER PUBLICATIONS

Ishihara et al., "Direct Condensation of Carboxylic Acids with Alcohols Catalyzed by Hafnium(IV) Salts," *Science*, vol. 290, pp. 1140-1142, Nov. 10, 2000.

Supplementary European Search Report for European Application No. EP 01 95 8409, completed on Dec. 17, 2003 and mailed on Jan. 14, 2004.

* cited by examiner

METHOD FOR PREPARING ESTER CONDENSATE

CROSS-REFERENCE TO RELATED APPLICATIONS

This application is a National Phase Application (35 USC 371) of PCT/JP01/07195 and claims priority of Japanese Application No. 2000-314712 filed Oct. 16, 2000.

TECHNICAL FIELD

The present invention relates to a method for preparing ester or thioester condensated by reacting carboxylic acid and alcohol or thiol, under the presence of a solvent using a tetravalent hafnium compound as a condensation catalyst.

BACKGROUND ART

The development of a chemical process being environment friendly is the highest priority issue in the present day, which the world community agrees also in the light of green chemistry (P. T. Anastas and J. C. Warner, Green Chemistry: Theory and Practice (Oxford University Press, Oxford, 1998). The esterification reaction is the most fundamental and important reaction of organic synthesis (Tetrahedron. 36, 2409, 1980). There are already an enormous amount of reports concerning the esterification reaction (Tetrahedron. 36, 2409, 1980), but in most of the cases, more than 1 equivalent weight of condensing agent or activating agent is used per substrate, there are problems such as a large quantity of by-product is produced after the reaction, thereby a complicated operation of separation and purification become necessary. Thus, it should actually be avoided in the light of green chemistry and atom efficiency. On the other hand, it would be an ideal process if a direct and catalytic esterification could be conducted from an equimolar amount of carboxylic acid and alcohol. But in most cases, ester can be obtained efficiently only if either carboxylic acid or alcohol is used excessively (Synthesis. 1978, 929, 1978; Chem. Lett. 1977, 55, 1977; Chem. Lett. 1981, 663, 1981; Synthesis. 1972, 628, 1972; Tetrahedron. Lett. 12, 3453, 1971; Tetrahedron. Lett. 14, 1823, 1973; Bull. Chem. Soc. Jpn. 54, 1276, 1981; Jpn. Patent Appl. 1980, No. 55-115570; Japanese Laid-Open Patent Application No. 52-75684; J. Am. Chem. Soc. 102, 7578, 1980; Tetrahedron. Lett. 28, 3713, 1987; J. Org. Chem. 56, 5307, 1991; Chem. Lett. 1981, 1671, 1981; Bull. Chem. Soc. Jpn. 62, 2353, 1989; Chem. Lett. 1984, 1085, 1984; J. Chem. Soc., Perkin Trans./ 1994, 3473, 1994).

Conventionally, a polyester polymerized catalyst wherein the catalyst is comprised of one or more metal compound selected from the group of scandium, yttrium, zirconium, hafnium, and vanadium, and one or more compound selected from a group comprising a compound having the structure of Ar—O— (Ar represents an aryl group) and the like (Japanese Laid-Open Patent Application No. 2000-154241) is known as polymerization catalyst. Additionally, as a method for preparing ester, wherein the catalyst activity is high, an ester is synthesized at a high yield even by using approximately an equimolar amount of acid and alkali which are the raw materials, a high reaction speed is obtained even at a low temperature, and being an excellent method in that a very small side reaction is produced, the following method for preparing ester (Japanese Laid-Open Patent Application No. 08-71429) is also known: the method uses an ester catalyst comprising a titanium metal compound selected from the group of titanium metal such as halides, nitrate salts, carboxylate salts, alcoholates and acetylacetone-type complex, as at least one of the active ingredients, and prepare ester from carboxylic acid and alcohol.

Moreover, as a method for preparing effectively carboxylic acid ester or carboxylic acid thioester from alcohol or thiol and carboxylic acid under a mild condition, the following method is known (Japanese Laid-Open Patent Application No. 05-286894): alcohol or thiol, or alternatively its ee1yl derivatives is reacted with an equivalent amount or a little smaller amount of carboxylic acid or carboxylic acid silyl ester, and when preparing carboxylic acid ester or carboxylic acid thioester, a carboxylic acid anhydride represented by a general formula $(R^6CO)_2O$ (wherein $R^6$ represents an aryl group that may have a substitute group) coexist with cationic catalyst of catalyst amount.

Recently, compounds having increasingly complicated structure and being unstable are used as drug medicine and the like, and a method of preparing ester or thioester that progresses smoothly from an equivalent amount of carboxylic acid and alcohol or thiol is anticipated in the light of composing drug medicine. An object of the present invention is to provide a method of preparing ester or thioester that can make: a catalytic esterification reaction from an equimolar amount of carboxylic acid and alcohol; or a catalytic thioesterification from carboxylic acid and thiol of which the amount is equimolar or a little smaller compared to carboxylic acid; and to provide a method that can be expected to be an industrial method that needs an enormous amount of synthesis in the light of green chemistry.

DISCLOSURE OF THE INVENTION

The present inventors have made a keen study to solve the above mentioned problems and have found that the hafnium chloride (IV), especially the tetravalent hafnium compounds as represented by hafnium chloride $(IV) \cdot (THF)_2$ or hafnium (IV)t-butoxide, have an excellent ability as a catalyst of direct condensation from an equimolar amount of carboxylic acid and alcohol, or thiol of which the amount is equimolar or a little smaller compared to carboxylic acid, and the present inventors have verified that said catalyst has a broad scope of application as a substrate. The present invention has thus been completed.

The present invention relates to a method for preparing ester condensate, wherein carboxylic acid and alcohol are reacted under the presence of a solvent, by using a tetravalent hafnium compound as a condensation catalyst; a method for preparing ester condensate, wherein the tetravalent hafnium compound is a hafnium chloride (IV); a method for preparing ester condensate according to claim 2, wherein the hafnium chloride (IV) is a hafnium chloride $(IV) \cdot (THF)_2$; a method for preparing ester condensate, wherein the tetravalent hafnium compound is a hafnium (IV) t-butoxide; a method for preparing ester condensate, wherein a polyester is synthesized by using polycarboxylic acid and multiple alcohol, or hydroxycarboxylic acid as the carboxylic acid and alcohol; a method for preparing ester condensate, wherein heating reflux is conducted by using a solvent, and azeotropic water is removed from the reaction system; a method for preparing ester condensate, wherein a nonpolar solvent is used as the solvent; a method for preparing ester condensate, wherein the nonpolar solvent is one or more solvent selected from toluene, xylene, or mesitylene; and a method for preparing ester condensate, wherein the reaction is conducted in a dried inactive gas atmosphere.

Furthermore, the present invention relates to a method for preparing thioester condensate, wherein carboxylic acid and thiol are reacted under the presence of a solvent, by using a tetravalent hafnium compound as a condensation catalyst; a method for preparing thioester condensate, wherein the tetravalent hafnium compound is a hafnium chloride (IV); a method for preparing thioester condensate, wherein the hafnium chloride (IV) is a hafnium chloride (IV)·(THF)$_2$; a method for preparing thioester condensate, wherein the tetravalent hafnium compound is a hafnium (IV)t-butoxide; a method for preparing thioester condensate, wherein a polythioester is synthesized by using polycarboxylic acid and polythiol as the carboxylic acid and thiol; a method for preparing thioester condensate, wherein heating reflux is conducted by using a solvent, and azeotropic water is removed from the reaction system; a method for preparing thioester condensate, wherein a nonpolar solvent is used as the solvent; a method for preparing thioester condensate, wherein the nonpolar solvent is one or more solvent selected from toluene, xylene or mesitylene; and a method for preparing thioester condensate, wherein the reaction is conducted in a dried inactivate gas atmosphere.

Additionally, the present invention relates to an esterification or thioesterification condensation catalyst comprising a tetravalent hafnium compound as an active ingredient; an esterification or thioesterification condensation catalyst, wherein the tetravalent hafnium compound is a hafnium chloride; (IV) an esterification or thioesterification condensation catalyst, wherein the hafnium chloride (IV) is a hafnium chloride (IV) (THF)$_2$ and an esterification or thioesterification condensation catalyst, wherein the tetravalent hafnium compound is a hafnium(IV)t-butoxide. dr

BEST MODE OF CARRYING OUT THE INVENTION

Figure 1:
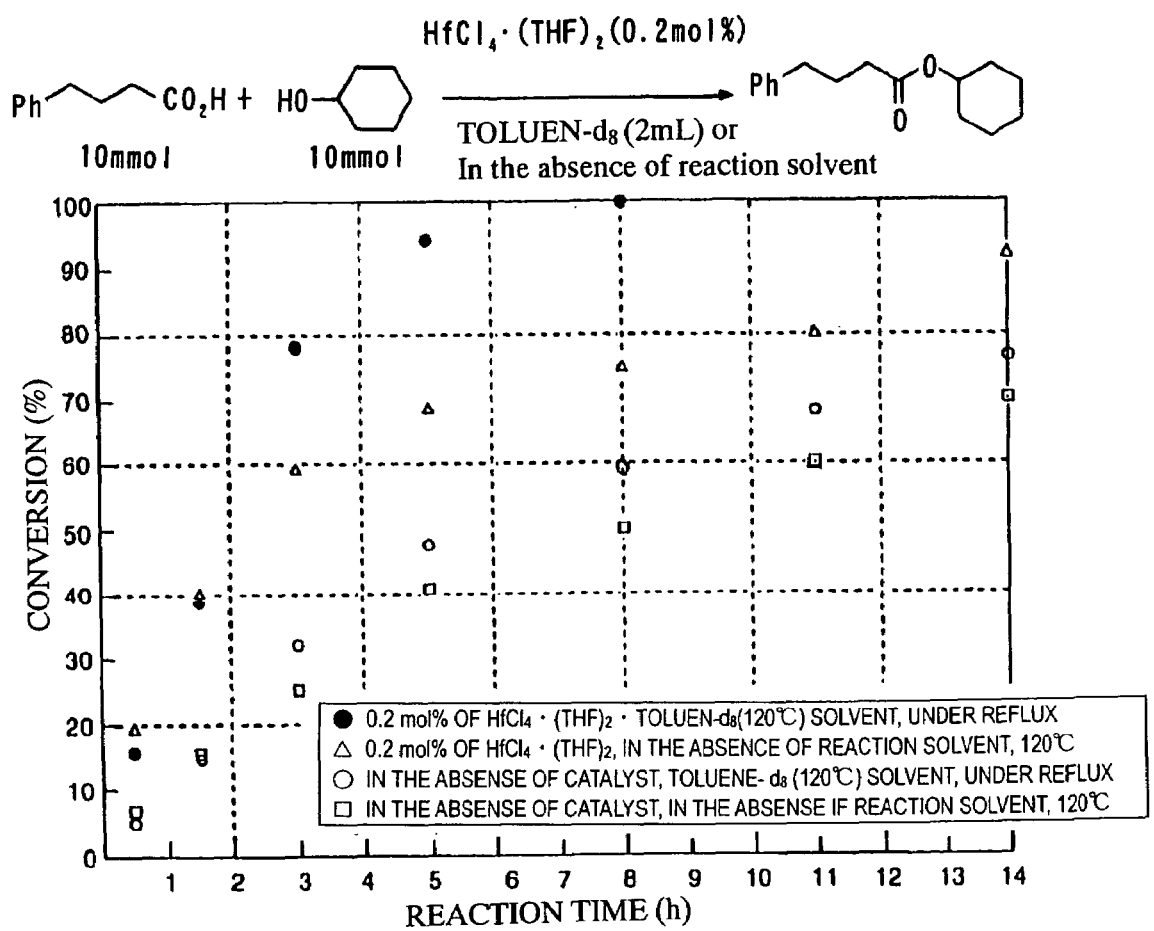
FIG. 1 represents the variation per hour of ester transformation of 4-phenyl butanoic acid and cyclohexanol, by using the hafnium chloride (IV)·(THF)$_2$, with the presence or absence of toluene.

As the method for preparing ester condensate of the present invention, there is no specific limitation as long as it is a method wherein a carboxylic acid and alcohol or thiol are reacted under the presence of a solvent, by using a tetravalent hafnium compound as a condensation catalyst. Specific examples of the tetravalent hafnium compound include: tetravalent hafnium halide salts such as hafnium chloride (IV) and the like; tetravalent hafnium carboxylic acid salts such as hafnium (IV) acetate and the like; tetravalent hafnium sulfate such as sulfate hafnium (IV) and the like; tetravalent hafnium alkoxides such as hafnium (IV)t-butoxide and the like; tetravalent alkyl hafnium (IV) compounds such as dicyclo pentadiene hafnium (IV) dichloride and the like; tetravalent hafnium (IV) compounds comprising a number of different ligands that are mentioned above; and the ether complex that are mentioned above. Among these examples, hafnium chloride (IV)·(THF)$_2$ that proceed ester transformation at a high yield, and is stable against humidity or the like is particularly preferable. As tetravalent hafnium compounds also comprising these hafnium chlorides (IV)·(THF)$_2$, commercial items or compounds synthesized by a common method can be used. There is no specific limitation to the amount of catalyst to be used of said tetravalent hafnium compounds, but in the case of synthesizing ester from carboxylic acid and alcohol, the amount is for example 0.1-1.0 mol %, preferably 0.1-0.2 mol %, and in the case of synthesizng thioester from carboxylic acid and thiol, the amount is for example 1-20 mol %, preferably 1-10 mol %.

As for the carboxylic acid used in the present invention, examples include: monocarboxylic acids such as caproic acid, capric acid, caprylic acid, lauric acid, myristic acid, oleic acid, stearic acid and the like; dicarboxylic acids such as fumaric acid maleic acid, malonic acid, adipic acid, terephthalic acid, isophthalic acid, sebacic acid, azelaic acid, dodecane dioic acid, diphenyl ether-4,4'-dicarboxylic acid and the like; tricarboxylic acids such as butane-1,2,4-tricarboxylic acid, cyclohexane-1,2,3-tricarboxylic acid, benzene-1,2,4-tricarboxylic acid, naphthalene-1,2,4-tricarboxylic acid and the like; tetracarboxylic acids such as butane-1,2,3,4-tetracarboxylic acid, cyclobutane-1,2,3,4-tetracarboxylic acid, benzene-1,2,4,5-tetracarboxylicacid, 3,3',4,4'-benzophenone tetracarboxylicacid, 3,3',4,4'-diphenylethertetracarboxylic acid and the like.

As for the alcohol used in the present invention, examples include: aliphatic monohydric alcohols such as methanol, ethanol, propanol, butanol, hexanol, heptanol, octanol, 2-ethylhexanol, decanol, dodecanol, stearyl alcohol and the like; alicyclic monohydric alcohols such as cyclohexanol and the like; aromatic monohydric alcohols such as benzyl alcohol and the like; multiple alcohols such as ethylene glycol, propylene glycol, neopentyl glycol, trimethyol propane, trimethylol ethane, pentaerythritol, dipentaerythritol, sorbitol, polyvinyl alcohol and the like.

As for the thiol used in the present invention, examples include: aliphatic thiols such as methane thiol, ethane thiol, propane thiol, butane thiol, hexane thiol, heptane thiol, octane thiol, decane thiol, dodecane thiol and the like; aromatic thiols such as thiophenol, 4-chlorothiophenol, 2-mercapto aniline and the like; polythiol such as 1,2-ethane dithiol, 2,2'-oxydiethanethiol, 2,2'-thiodiethanethiol, 1,3-propane dithiol, 1,4-butane dithiol, 1,5-pentane dithiol, 1,6-hexane dithiol, 1,9-nonoic dithiol, pentaerythrithiol, cyclo hexane thiol, cyclo hexane dithiol, xylylene dithiol, benzene dithiol, toluene dithiol, polytetra methylene dithiol, 1,2-benzene dimethane thiol, 1,3-benzene methane thiol, 1,4-benzene methane thiol, 1,2,6-hexane triol trithioglycolate and the like.

As for the method for preparing the ester condensate of the present invention, an equimolar carboxylic acid and alcohol are to be used. Therefore, when monohydric carboxylic acid and monohydric alcohol are used respectively as said carboxylic acid and alcohol, an ester monomer is obtained, and when using polycarboxylic acid such as α,ω-alphatic dicarboxylic acid and the like, and multiple alcohol such as α,ω-aliphatic diol and the like, polyester can be synthesized. Furthermore, polyester can be synthesized also when ω-hydroxycarboxylic acid is used as carboxylic acid and alcohol. Examples for ω-hydroxycarboxylic acid include: ω-hydroxyundecanoic acid, hydroxydodecane acid, p-hydroxybenzoic acid, m-hydroxybenzoic acid, 6-hydroxynaphthalene-2-carboxylic acid, 4-(p-hydroxyphenoxy) benzoic acid, 3-(p-hydroxyphenoxy) benzoic acid, 4-(m-hydroxyphenoxy) benzoic acid, 3-(m-hydroxyphenoxy) benzoic acid and the like. As for the method for preparing the thioester condensate of the present invention, carboxylic acid and an equimolar or a little more amount of thiol are to be used. Therefore, when monohydric carboxylic acid and thiol are used respectively as said carboxylic acid and thiol, a thioester monomer is obtained, and when using the above mentioned polycarboxylic acid and polythiol are used, polyester can be synthesized.

There is no specific limitation to the solvent used for the present invention, and it can be exemplified by a polar solvent, a mixed solvent of polar solvent and nonpolar solvent, and a nonpolar solvent. However, a nonpolar solvent is preferable in light of the easiness of removing the water that the esterification and thioesterification reaction generates, outside of the reaction system. In other words, it is preferable to use nonpolar solvent such as toluene to conduct heating reflux, and to remove easily azeotropic water from the reaction system. As to the method for removing said water, it can be exemplified by the method using known dehydrating agents such as calcium hydride or molecular sieves but they are not limited to these examples. Examples of the above-mentioned nonpolar solvents include toluene, xylene, mesitylene, pentamethylbenzene, m-terphenyl, benzene, ethylbenzene, 1,3,5-tri-isopropyl benzene, o-dichlorobenzene, 1,2,4-trichlorobenzene, naphthalene, 1,2,3,4-tetrahydronaphthalene (tetralin). Examples of polar solvent include ethers such as anisole, THF, 1,4-dioxane and the like, and others such as N-methyl-2-pyrrolidinone (N-methyl-2-pyrrolidone), N-butyl-2-pyrrolidinone (N-butyl-2-pyrrolidone), N-ethyl-2-pyrrolidone, 1,3,dimethyl-2-pyrrolidone, cresol, N,N-dimethylformamide, dimethyl acetamide, hexamethyl phosphoramide, dimethyl sulfoxide, diphenyl sulfone, nitrobenzene, benzonitrile, 1,3-dimethyl-2-imidazolidinone, γ-butyrolactone, phenol and the like. Moreover, when using volatile alcohol such as methanol and the like as a substrate, said alcohol has an action also as a solvent, thus no other solvent has to be used.

As for the condensation reaction in the method for preparing the ester or thioester condensate for the present invention, it is preferable to let occur the reaction in a dried inactivate gas atmosphere, for example in an argon or nitrogen atmosphere. In the argon atmosphere, it is preferable to conduct the condensation reaction by flowing the argon, and by keeping the argon atmosphere during the reaction, it is possible to obtain dehydration and deoxydization atmospheres at the same time. For the ester condensation reaction such as a condensation reaction condensing monohydric carboxylic acid with monohydric alcohol, a polycondensation reaction polycondensing aliphatic polycarboxylic acid with aliphatic multiple alcohol, or for the thioester condensation reaction such as a condensation reaction condensing monohydric carboxylic acid with monohydric thiol, or a polycondensation reaction polycondensing aliphatic polycarboxylic acid with aliphatic polythiol, it is preferable to conduct the reaction under heating reflux between 100 to 200.degree. C., particularly preferable between 120 to 160.degree. C. for 1 to 24 hours. On the other hand, for a condensation reaction condensing aromatic carboxylic acid with aromatic alcohol or aromatic thiol, or a polycondensation reaction polycondensing aromatic carboxylic acid with aromatic alcohol or aromatic thiol, it is preferable to conduct the reaction under heating reflux between 120 to 250.degree. C., particularly preferable between 150 to 200.degree. C. for 24 to 72 hours. The purification of the monomer ester or polyester, or the monomer thioester or polythioester obtained by these condensation reaction or polycondensation reaction, can be carried out by the known method. Furthermore, according to the present invention, by using equimolar amount of carboxylic acid and alcohol or carboxylic acid and a little more amount of thiol, no side reaction occurs, thus the purification is very simple compared to the conventional method.

The present invention will be described in detail by the following examples, while the technical scope of the present invention will not be limited to these examples.

EXAMPLE 1

Selection of Tetravalent Hafnium Compound

The esterification reaction of 4-phenyl butanoic acid (1 equivalent) and benzyl alcohol (1 equivalent) in a toluene solvent (5 ml) was selected as a model reaction, and under the argon atmosphere, heating reflux at 120.degree. C. for 1.5 hours was conducted and the catalyst activity of various metallic salts (10 mol %) were compared (reaction condition A). The water generated by the reaction was removed by the calcium hydride in the Soxhlet tube attached to the top of the reaction flask. The results are shown in Table 1. The hafnium chloride (IV) and the zirconium chloride (IV) (Chem. Lett. 1981, 1671, 1981; Bull. Chem. Soc. Jpn. 62, 2353, 1989) showed a similar high catalyst activity against this esterification reaction. The hafnium (IV) t-butoxide also showed a similar high catalyst activity, but the zirconium (IV) ethoxide was inactive. The test was also executed for titanium (IV) salt (Jpn. Patent Appl. 1980, No. 55-115570, Japanese Laid-Open Patent Application No. 52-75684) or tin (IV) salt (J. Am. Chem. Soc. 102, 7578, 1980; Tetrahedron. Lett. 28, 3713, 1987; J. Org. Chem. 56, 5307, 1991), already described as a esterification catalyst, and it was shown that these catalyst reaction were lower compared to the hafnium (IV) or the zirconium (IV) salt. The test was also executed for other various metallic salts or organic metallic compounds, $3,4,5-F_3C_6H_2B(OH)_2$(J. Org. Chem. 61, 4196, 1996; Macromolecules. 33, 3511, 2000), $BCl_3$ (Synthesis. 1972, 628, 1972; Tetrahedron. Lett. 12, 3453, 1971), $AlCl_3$ (Tetrahedron. Lett. 14, 1823, 1973), $SiCl_4$(Bull. Chem. Soc. Jpn. 54, 1276, 1981), $ScCl_3$, $Sc(OTf)_3$ (The model reaction indicated in Table 1 using $Sc(OTf)_3$ as a catalyst gave α-tetralone as a major product., J. Am. Chem. Soc. 117, 4413 and 6639(corrections), 1995; J. Org. Chem. 61, 4560, 1996; Synthesis. Lett. 1996, 265, 1996), $FeCl_3$, $CoCl_2$, $NiCl_2$, $ZnCl_2$, $GaCl_3$, $GeCl_4$, $SbCl_5$, $LaCl_3$, $PbCl_2$, but all of these showed very low activity or no activity at all.

Next, some metallic salts that showed catalyst activity in the above mentioned experiment were selected, and to determine which of said metallic salts show high catalyst turnover frequency (TOF), the aforementioned reaction was executed by heating reflux for 12 hours under the presence of 1 mol % of catalyst (reaction condition B). In result, it was found that when the hafnium chloride (IV)·$(THF)_2$ and the hafnium (IV) t-butoxide were used as a catalyst, the reaction proceed quantitatively. In contrast, using zirconium (IV) salt and tin (IV) salt gave the relevant ester at a low yield. It was interesting to note that using tin (IV) salt gave a better result compared to other metallic chloride salts except hafnium (IV) and metallic alcoxide. In consequence, it was found that hafnium (IV) compound was the most effective metallic catalyst for this direct esterification condensation.

TABLE 1

Ph~~~CO₂H + Ph~OH →(catalyst, toluene, azeotropic reflux) Ph~~~C(=O)O~Ph

| catalyst | yield under the reaction condition A (%) | yield under the reaction condition B (%) |
| --- | --- | --- |
| SnCl₄ | 34 | 48 |
| TiCl₄ | 28 | 73 |
| Ti(Oi-Pr)₄ | 34 | 82 |
| ZrCl₄ | 77 | — |
| ZrCl₄•(THF)₂ | 84 | 38 |
| Zr(OEt)₄ | 0 | — |
| HfCl₄ | 83 | — |
| HfCl₄•(THF)₂ | 82 | >99 |
| Hf(Ot-Bu)₄ | 82 | >99 |
| HfO₂ | <5 | — |

EXAMPLE 2

Optimization of the Reacting Solvent

To remove the water produced in the reaction and to optimize the reacting solvent, the variation per hour of the esterification reaction was observed by changing some reaction conditions such as the presence or the absence of the reacting solvent, with the esterification reaction of 4-phenyl butanic acid and cyclo hexanol, under the presence of 0.2 mol % (9.3 mg) of hafnium chloride(IV)·(THF)₂. The results are shown in Table 1. The direct condensation reaction of 4-phenyl butanoic acid and cyclohexanol produces cyclohexyl-4-phenylbutyrate, and the conversion rate of said cyclohexyl-4-phenylbutyrate was obtained by ¹H NMR analysis. From these results, it was found that it is the best method to use toluene solvent to conduct heating reflux, and to dehydrate azeotropic water with calcium hydride or molecular sieves 4A in the Soxhlet tube attached to the top of the reaction flask. On the other hand, when the reacting mixture was heated without using a solvent, it was shown that the reaction speed began to decrease after a lapse of about 2 hours. This tendency was also observed when the reaction was conducted without using a catalyst. From these results of the experiments, it was found that in order to conduct effective esterification reaction, azeotropic dehydration using a reacting solvent is most effective. This means that both the activity of the catalyst itself and the effectiveness of the removal of water are important factors to aim the improvement of the reaction efficiency.

EXAMPLE 3

Scope of Substrate Application

By combining diversely the carboxylic acid of various structure and alcohol, the scope of substrate application of the tetravalent hafnium compound was examined. A Soxhlet tube filled with dried molecular sieves 4A (about 1.5 g) was connected to the top of a 5 ml eggplant flask contained with a teflon coated magnetic stirrer, and a cooling tube was further attached over said Soxhlet tube. Unless there is a particular point of concern, toluene solvent (2 ml) and 0.1 mol %, 0.2 mol % or 1 mol % of hafnium chloride (IV)·(THF)₂ were added to carboxylic acid (10 mmol) and alcohol (10 mmol), and heating reflux was conducted in the argon for several hours at 120.degree.C. After the reaction, the mixture solution was purified by direct silica gel column chromatography (eluant hexane:ethyl acetate=4:1 to 8:1), and the solution was dried under reduced pressure. The results are shown in Table 2. In Table 2, the following are shown: for the experiment of Entry 3, toluene solvent (5 ml) was used; for the experiment of Entry 4, 4-phenyl butanoic acid (36 mmol) and toluene solvent (4 ml) were used; for the experiment of Entry 5, the numerical value of yield showed in parenthesis is the value in the case the inventors wanted to use the catalyst; for the experiment of Entry 9, o-xylene solvent (2 ml) was used; for the experiment of Entry 14, enantiomer of carboxylic acid was used and at a yield of 84%, the enantiomer of ester was obtained; for the experiment of Entry of 17, 1,3,5-mesitylene solvent (2 ml) was used; for the experiments of Entry 18 and 19, the lactone value is shown for the yield.

TABLE 2

R¹CO₂H + R¹OH →(HfCl₄·(THF)₂, toluene, azeotropic reflux) R¹CO₂R²

| entry | RCO₂H | ROH | HfCl₄•(THF)₂ (1 mol %) | reaction time (h) | yield (%) |
| --- | --- | --- | --- | --- | --- |
| 1 | Ph~~~CO₂H | Ph—≡—OH | 0.2 | 6 | 97 |
| 2 | Ph~~~CO₂H | Ph~=~OH | 0.2 | 24 | 92 |
| 3 | Ph~~~CO₂H | Ph~OH | 0.1 | 18 | >99 |
| 4 | Ph~~~CO₂H | EtC(CH₂OH)₃ | 0.2 | 24 | >99 |
| 5 | Ph~~~CO₂H | cyclohexyl-OH | 0.2 | 5 | 94 (36) |

TABLE 2-continued $$R^1CO_2H + R^1OH \xrightarrow[\text{azeotropic reflux}]{\text{HfCl}_4 \cdot (\text{THF})_2 \atop \text{toluene,}} R^1CO_2R^2$$

| entry | RCO$_2$H | ROH | HfCl$_4$•(THF)$_2$ (1 mol %) | reaction time (h) | yield (%) |
|---|---|---|---|---|---|
| 6 | Ph~~~CO$_2$H | l-menthol | 0.2 | 36 | >99 |
| 7 | Ph~~~CO$_2$H | Ph-CH(OH)-CH$_3$ | 0.2 | 13 | >99 |
| 8 | Ph~~~CO$_2$H | Et$_3$COH | 1.0 | 24 | 0 |
| 9 | Ph~~~CO$_2$H | PhOH | 0.2 | 36 | 91 |
| 10 | Ph-CH=CH-CO$_2$H | Ph~OH | 0.2 | 10 | 92 |
| 11 | p-NO$_2$C$_6$H$_4$~CO$_2$H | Ph~OH | 0.1 | 18 | 98 |
| 12 | cyclohexyl-CO$_2$H | Ph~OH | 0.2 | 7 | 96 |
| 13 | Et$_2$CHCO$_2$H | Ph~OH | 0.2 | 60 | 98 |
| 14 | Ph-CH(OMe)-CO$_2$H | Ph~OH | 0.2 | 13 | 98 |
| 15 | PhCO$_2$H | Ph~OH | 0.2 | 15 | 92 |
| 16 | adamantyl-CO$_2$H | Ph~OH | 0.2 | 10 | 92 |
| 17 | PhCO$_2$H | 3,5-Me$_2$C$_5$H$_3$OH | 1.0 | 24 | 95 |
| 18 | HO$_2$C~~~OH | | 0.2 | 10 | 96 |
| 19 | HO$_2$C~~~~OH | | 0.2 | 10 | 94 |

As it is also shown in Table 2, every carboxylic acid reacted with primary and secondary alcohol, under the presence of the catalyst of 0.2 mol % and under, and produced ester quantitatively, but as it is shown from the experiment of Entry 8, it did not react with tertiary alcohol. Furthermore, as it is shown from the experiment of Entry 17, the aromatic substrates (benzoic acid and phenol) showed lower reactivity compared to aliphatic substrates, and when carboxylic acid and alcohol are both aromatics, the ester could be obtained at a high yield, by increasing the catalyst amount up to 1 mol %. Moreover, when the reactivity is low, it is also effective to use a benzene solvent of higher boiling point, for example, o-xylene of the experiment of Entry 9 or 1,3,5-mesitylene of the experiment of Entry 17 and to conduct heating reflux.

EXAMPLE 4

Use of Volatile Alcohol as a Solvent

The catalyst activity of hafnium chloride (IV)·(THF)$_2$ in the esterification reaction of carboxylic acid with volatile alcohol such as methanol was studied. A Soxhlet tube filled with dried molecular sieves 4A (about 1.5 g) was connected to the top of a 5 ml eggplant flask contained with a teflon coated magnetic stirrer, and a cooling tube was further attached over said Soxhlet tube. As it is shown in the following equation, 1 mol % of hafnium choloride (IV)·(THF)$_2$ was added to the carboxylic acid (10 mmol) and methanol (10 mmol), and heating reflux was conducted in the argon for several hours at room temperature. As a result, ester was obtained at a yield of 99%.

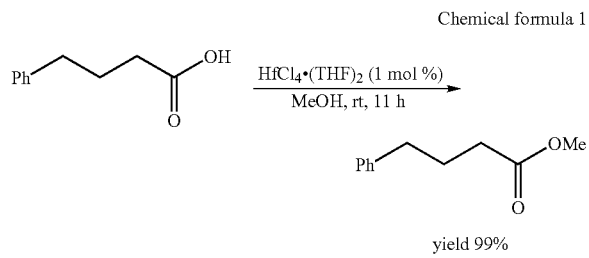

Chemical formula 1 yield 99%

EXAMPLE 5

Catalyst Action of Hafnium (IV) and Titanium (IV)

Titanium (IV) compound is known to be effective also as a catalyst used in the ester exchange reaction of ester and alcohol (J. Polym. Sci., Part A, Polym. Chem. 26, 2199, 1988). Therefore, the action of catalyst for hafnium (IV) and titanium (IV) was studied by the esterification exchange reaction shown by the following equation. $TiCl_4$ showed an ester exchange reaction at a yield of 98%, however, it is interesting to note that $HfCl_4 \cdot (THF)_2$ did not show the ester exchange reaction under the same reaction condition. This indicates that the catalyst action of the hafnium (IV) and the titanium (IV) differs by nature (J. Polym. Sci., Part A, Polym. Chem. 26, 2199, 1988). The difference between the two substances can be explained by the difference of the activated intermediate of the esterification reaction being hafnium (IV) carboxylate and titanium (IV) alkoxide, but the details are not clear.

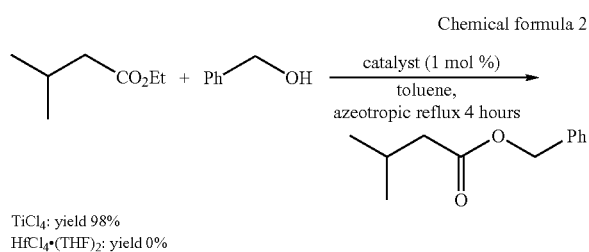

Chemical formula 2

$TiCl_4$: yield 98%
$HfCl_4 \cdot (THF)_2$: yield 0%

EXAMPLE 6

Composition of Polyester

By using the effect of the hafnium (IV) compound as an esterification catalyst, the synthesis of polyester shown in Table 3 was studied (S. R. Sandler and W. Karo, Polymer Synthesis, 2nd ed. (Academic Press: San Diego, 1992) Vol. 1, Chapter 2). A Soxhlet tube filled with dried molecular sieves 4A (about 1.5 g) was connected to the top of a 5 ml eggplant flask contained with a teflon coated magnetic stirrer, and a cooling tube was further attached over said Soxhlet tube. 10 mmol of hydroxycarboxylic acid, 2 ml of o-xylene and 0.2 mol % of hafnium chloride (IV)·(THF)$_2$ were added and heating reflux was conducted in the argon for 24 hours. After the reaction, a solution wherein the mixture solution was dissolved into 30 ml of chloroform was poured into 150 ml of acetone while being stirred. The white precipitation that was produced, was collected by filtration, and dried under reduced pressure. Furthermore, by the same method, 10 mmol of dicarboxylic acid, 10 mmol of diol, 2 ml of o-xylene and 0.2 mol % of hafnium chloride (IV)·(THF)$_2$ were added and heating reflux was conducted in the argon for 24 hours. After the reaction, the mixture solution was dissolved in 200 ml of chloroform, and 30 ml of methanol was added. The mixture solution was concentrated, the white precipitation thus produced was collected by filtration, and dried under reduced pressure.

The results are shown in Table 3. In Table 3, the following are shown: the yield represents isolated yield; DP stands for the degree of polymerization; DP and the number average molecular weight (Mn) are values obtained by $^1$H NMR; the weight-average molecular weight (Mw) is the value wherein gel permeation column chromatography (two columns of Two linear TSK-gel-GMX$_{XL}$ (Tosoh Corporation) connected in series were used) is conducted to 0.2% by weight of the generated polymer in THF at 40.degree. C., with polystyrene as a standard; the value in parenthesis for HO [CO(CH$_2$)$_{11}$ O]$_n$H is a value of thermal polymerization condensation in the absence of catalyst; the various values for polyester in the bottom line are the values obtained by using 1 mol % of hafnium chloride (IV)·(THF)$_2$ and conducting the reaction for 4 days. These results revealed that the hafnium chloride (IV)·(THF)$_2$ is useful as a catalyst for polycondensation reaction in the method for preparing polyester using ω-hydroxycarboxylic acid or the method for preparing polyester using α,ω-aliphatic dicarboxylic acid and α, ω-aliphatic diol.

TABLE 3

| polyester | isolated yield (%) | DP | $M_n \times 10^4$ | $M_w \times 10^4$ |
|---|---|---|---|---|
| HO[CO(CH$_2$)$_9$O]$_n$H | 95 | >200 | 1.82 [>3.40] | 3.40 |
| HO[CO(CH$_2$)$_{11}$O]$_n$H | 97 | >200 | 2.77 [>3.96] | 7.24 |
|  | (88) | (45) | -[(0.89)] | — |
| HO[CO(CH$_2$)$_2$CO$_2$(CH$_2$)$_6$O]$_n$H | 98 | >200 | 2.24 [>4.00] | 3.87 |
| HO[CO(CH$_2$)$_7$CO$_2$(CH$_2$)$_{10}$O]$_n$H | 97 | >200 | 2.69 [>6.52] | 5.83 |
|  | 96 | >200 | 1.34 [>6.09] | 6.51 |

EXAMPLE 7

Synthesis of Thioester Using the Catalyst of Hafnium Chloride (IV)·(THF)$_2$

By using the catalyst of hafnium chloride (IV)·(THF)$_2$, the thioester composition reaction from carboxylic acid and thiol was studied. A Soxhlet tube filled with dried molecular sieves 4A (about 1.5 g) was connected to the top of a 5 ml eggplant flask contained with a teflon coated magnetic stirrer, and a cooling tube was further attached over said Soxhlet tube. As shown in the following equation, toluene solvent (2 ml) was added to carboxylic acid (20 mmol) and benzyl thiol (24 mmol), and under the presence or in the absence of 5 mol % of hafnium chloride (IV)·(THF)$_2$, heating reflux was conducted in the argone for 24 hours at 120.degree. C. After the reaction, the mixture solution was purified directly by silica gel column chromatography (eluant hexane: ethylacetate=40:1), and dried under a reduced pressure. The results are shown in Table 4. Furthermore, decane thiol ($C_{10}H_{21}SH$) was used instead of benzyl thiol, and under the presence of 5 mol % of hafnium chloride (IV)·(THF)$_2$ in the same manner as described above, heating reflux was conducted in the argone for 17 hours at 120.degree. C. The results are also shown in Table 4. As also shown in Table 4, under the presence of hafnium chloride (IV)·(THF)$_2$, thioester was obtained at a high yield. These results revealed that hafnium (IV) compounds such as hafnium chloride (IV)·(THF)$_2$ and the like are useful as a catalyst for thioester synthesis reaction.

TABLE 4

Ph∼∼∼CO$_2$H + RSH (1.2 eq.) $\xrightarrow{\text{HfCl}_4\text{(THF)}_2}{\text{Toulen, MS4A, azeotropic reflux}}$ Ph∼∼∼C(=O)SR

| Entry | R | catalyst (mol %) | reaction time (h) | yield (%) |
|---|---|---|---|---|
| 1 | benzyl | 5 | 24 | 97 |
| 2 | benzyl | 0 | 24 | small |
| 3 | $C_{10}H_{21}$ | 5 | 17 | >99 |

INDUSTRIAL APPLICABILITY

According to the present invention, conducting esterification or thioesterification reaction by direct condensation in a nonpolar solvent, with the use of tetravalent hafnium compound, does not produce any by-product, the separation and purification operation of ester and thioester is easy, and it is particularly preferable for a reaction of a huge scale. Furthermore, when the hafnium chloride (IV)·(THF)$_2$, which is particularly stable against humidity and the like, is used as a tetravalent hafnium compound, said hafnium chloride (IV)·(THF)$_2$ shows excellent catalyst activity for ester or thioester condensation and ester or thioester polycondensation, and can synthesize ester, polyester, thioester polythioester and the like, at a high-efficiency.

The invention claimed is:

1. A method for preparing ester condensate comprising, reacting carboxylic acid and alcohol in the presence of a solvent, and adding a tetravalent hafnium chloride (IV)·(THF)$_2$ as a condensation catalyst.

2. A method for preparing thioester condensate comprising, reacting carboxylic acid and thiol in the presence of a solvent, and adding a tetravalent hafnium chloride (IV)·(THF)$_2$ as a condensation catalyst.

3. The method for preparing thioester condensate according to claim 2, wherein the thioester condensate is a polythioester, wherein the carboxylic acid is polycarboxylic acid, and wherein the thiol is a polythiol.

* * * * *